United States Patent [19]
Plyley et al.

[11] Patent Number: 5,152,754
[45] Date of Patent: Oct. 6, 1992

[54] TROCAR

[75] Inventors: Alan K. Plyley, Santa Barbara; John M. Barker, Ventura; Claude Vidal, Santa Barbara; Russell J. Redmond, Goleta, all of Calif.

[73] Assignee: Minnesota Mining and Manufacturing Company, St. Paul, Minn.

[21] Appl. No.: 657,105

[22] Filed: Feb. 15, 1991

[51] Int. Cl.⁵ .............................................. A61M 5/178
[52] U.S. Cl. ...................................... 604/164; 606/185
[58] Field of Search ............... 604/760, 161, 164, 165, 604/766–769, 272–274; 606/184–185, 171; 128/751, 752, 753, 754

[56] References Cited

U.S. PATENT DOCUMENTS

| | | |
|---|---|---|
| 1,527,291 | 2/1925 | Zorraquin . |
| 2,001,638 | 5/1935 | Tornsjo . |
| 2,623,521 | 12/1952 | Shaw . |
| 2,630,803 | 3/1953 | Baran . |
| 3,713,447 | 1/1973 | Adair . |
| 3,774,604 | 11/1973 | Danielsson . |
| 3,789,852 | 2/1974 | Kim et al. . |
| 4,168,699 | 9/1979 | Hauser . |
| 4,177,814 | 12/1979 | Knepshield et al. . |
| 4,190,048 | 2/1980 | Sampson . |
| 4,403,617 | 9/1983 | Tretinyak . |
| 4,431,426 | 2/1984 | Groshong et al. . |
| 4,535,773 | 8/1985 | Yoon ................................ 604/51 |
| 4,601,710 | 7/1986 | Moll ................................ 604/165 |
| 4,617,929 | 10/1986 | Gill . |
| 4,617,933 | 10/1986 | Hasson . |
| 4,654,030 | 3/1987 | Moll et al. .................. 604/165 |
| 4,747,831 | 5/1988 | Kulli ............................ 604/110 |
| 4,808,168 | 2/1989 | Warring et al. .............. 604/158 |
| 4,813,426 | 3/1989 | Haber et al. . |
| 4,902,280 | 2/1990 | Lander ........................ 604/165 |
| 4,906,236 | 3/1990 | Alberts et al. . |
| 4,922,602 | 5/1990 | Mehl . |
| 4,931,042 | 6/1990 | Holmes et al. ............... 604/164 |
| 4,952,207 | 8/1990 | Lemieux . |
| 5,030,206 | 7/1991 | Lander . |
| 5,066,288 | 11/1991 | Deniega et al. . |
| 5,104,382 | 4/1992 | Brinkerhoff et al. . |
| 5,114,407 | 5/1992 | Burbank . |
| 5,116,353 | 5/1992 | Green . |

FOREIGN PATENT DOCUMENTS

| | | |
|---|---|---|
| 0135354 | 8/1984 | European Pat. Off. . |
| 0265193 | 4/1988 | European Pat. Off. . |
| 0350291 | 7/1989 | European Pat. Off. . |

OTHER PUBLICATIONS

"The Source of laparoscopic innovation", by Origin Medsystems, Inc., Four (4) Pages, dated 1992.

Primary Examiner—C. Fred Rosenbaum
Assistant Examiner—M. Mendez
Attorney, Agent, or Firm—Gary L. Griswold; Walter N. Kirn; Jeffrey J. Hohenshell

[57] ABSTRACT

A trocar for placement in the lumen of a cannula to facilitate inserting the cannula through the wall of a body cavity, the trocar comprising an obturator with a point for piercing the wall of the body cavity, and a protective sleeve mounted concentrically around the obturator. The obturator retracts proximally relative to the protective sleeve after the trocar point has penetrated through the wall of the body cavity. The protective sleeve is mounted for axial movement relative to the obturator, retracting proximally in response to drag from the wall of the body cavity as the trocar is advanced through the wall, and advancing distally after the cannula has penetrated through the wall, reducing the drag on the sleeve. The distal advancement of the sleeve triggers the retraction of the obturator.

17 Claims, 4 Drawing Sheets

FIG. 5. FIG. 6.
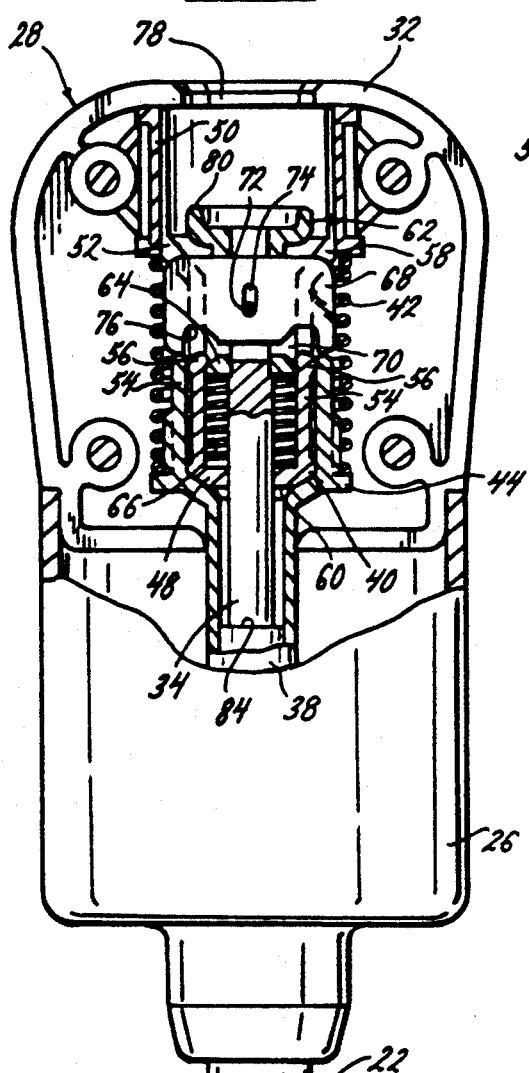
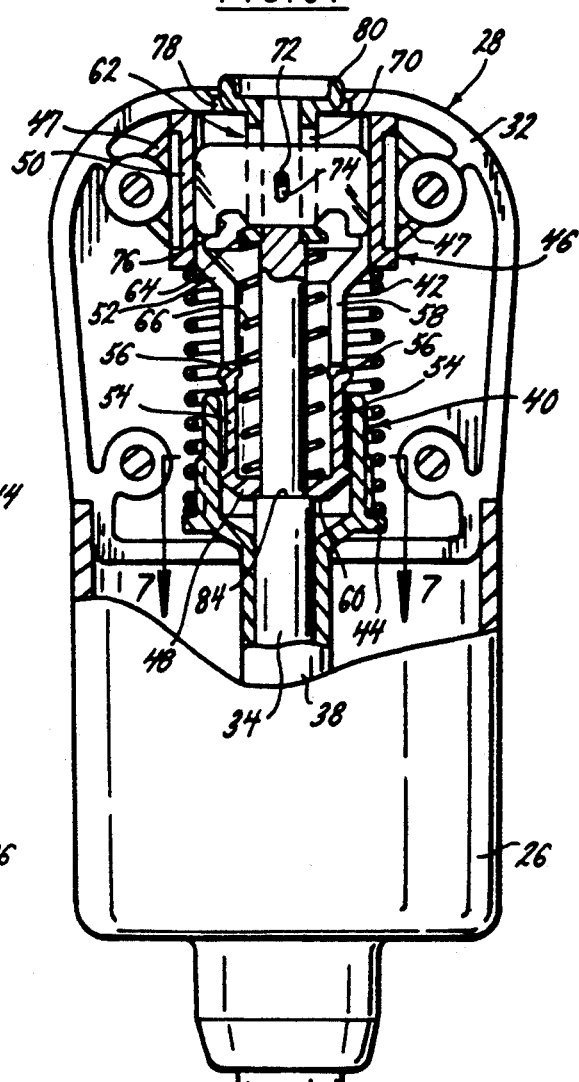
FIG. 7.
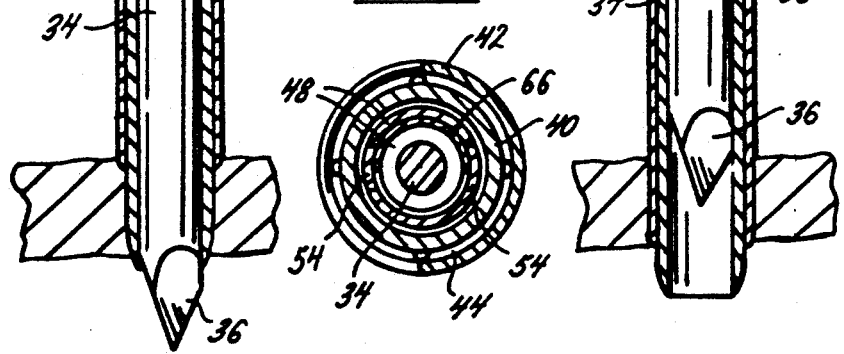

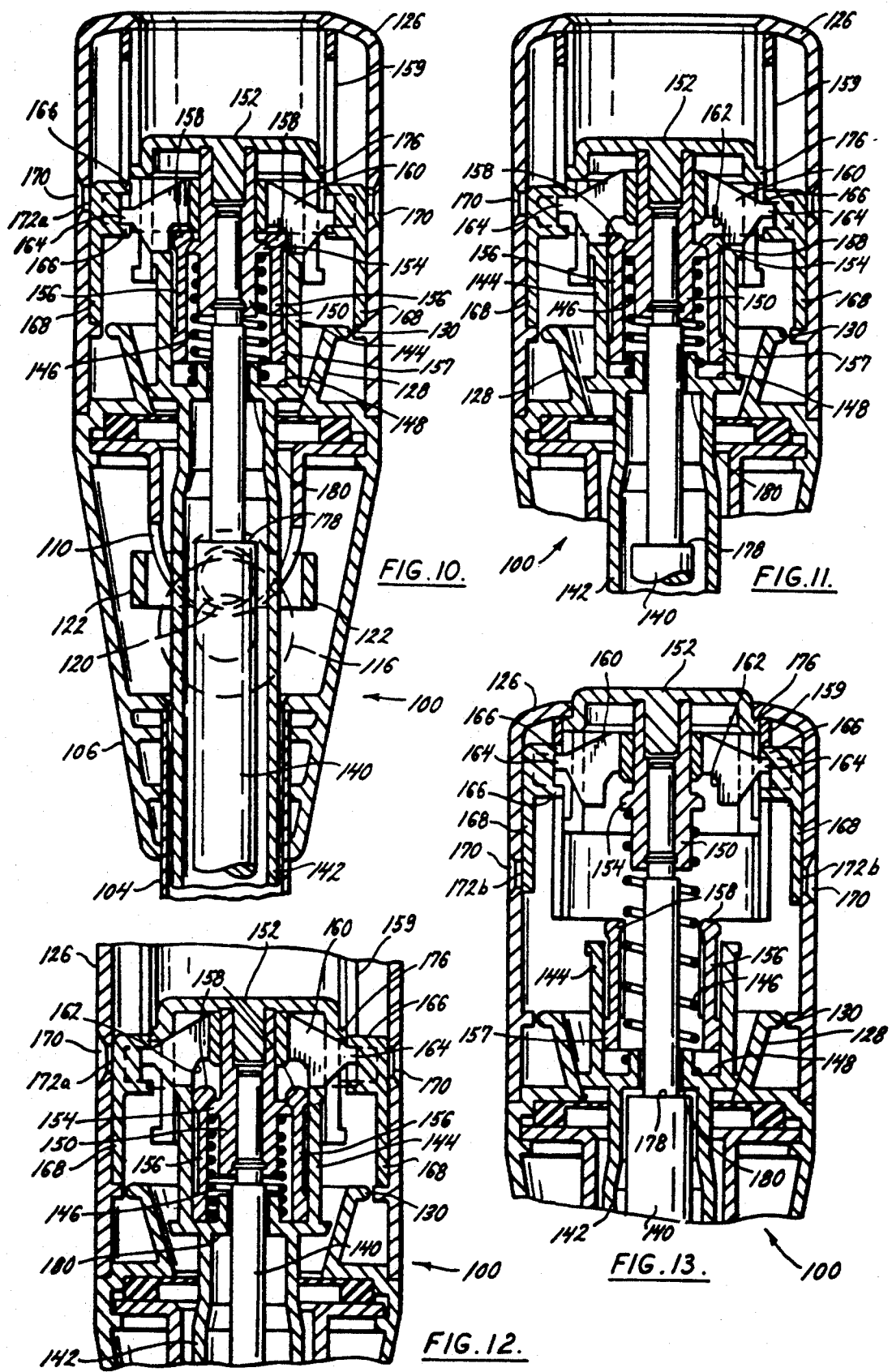

TROCAR

BACKGROUND AND SUMMARY OF THE INVENTION

This invention relates to a trocar, and in particular to a trocar with a retractable point to reduce the risk of injuring internal organs during use.

An increasing number of abdominal surgical procedures are being performed with laparoscopic techniques in order to avoid a large skin incision. Typically in laparoscopic surgery, a special needle, similar to the pneumoneedle described in U.S. Pat. No. 4,808,168, is inserted through the skin, and used to inflate the abdominal cavity with $CO_2$. Once the abdomen is adequately dilated, the needle is removed and a rigid access tube with a larger diameter (for example 10 or 11 mm) is passed through the skin in the same location. The tube provides access for the laparoscope, a small diameter cylindrical viewing device that allows the surgeon to see inside the abdomen. To drive the tube through the skin, the surgeon places a trocar in the lumen of the tube to provide a sharp leading cutting edge.

The trocar devices presently available, for example those shown in U.S. Pat. Nos. 4,535,773, 4,601,710, 4,654,030, 4,902,280, and 4,931,042, typically comprise a sharp point for penetrating the skin, surrounded by a spring-loaded protective sleeve. As these trocar devices are urged through the skin, friction with the skin causes the protective sleeve to slide proximally (rearwardly). After the access tube has penetrated through the skin, there is no longer friction between the protective sleeve and the skin, and the spring urges the protective sleeve distally (forwardly) to cover the sharp point, locking the protective sleeve in position to reduce the risk of accidental puncture of the underlying organs. These prior art trocars rely on a similar principle of operation: The friction or drag on the protective sleeve as the trocar is advanced through the skin pushes the protective sleeve back to expose the sharp point. Once the access tube has penetrated the skin, the drag on the protective sleeve is reduced and the sleeve accelerates distally (forwardly) under the bias of the spring to cover the point. A significant amount of force usually must be applied to penetrate the skin (particularly the tough facia), and it is often difficult for the surgeon to determine precisely when the skin has been penetrated, and therefore the trocar may continue to advance toward the underlying organs after it has penetrated the skin. Thus, the protective sleeve must "catch up" to the moving trocar point before the trocar reaches the underlying organs.

The trocar of the present invention provides a mechanism for retracting the trocar point upon penetration of the skin. Thus, the sharp trocar point begins to move away from the underlying organs upon penetration of the skin. Moreover, because of the proximal (rearward) motion of the point, the covering of the point is not dependent upon the sleeve "catching up" with the point as in the prior art trocars where only the sleeve moves. The trocar of the present invention can also provide a positive tactile signal, conveniently triggered by the retraction of the point, indicating when the trocar has penetrated the skin, so that the surgeon can stop advancing the trocar.

The trocar device of the present invention is of the type placed in the lumen of a cannula to facilitate inserting the cannula through the wall of a body cavity. The trocar generally comprises a point for piercing the wall of the body cavity, a protective sleeve mounted concentrically around the point for axial movement relative to the point, and means for biasing the protective sleeve distally (forwardly) relative to the point so that after the point penetrates the wall of the body cavity, the sleeve moves distally under the bias. The trocar of the present invention further comprises means for retracting the point relative to the protective sleeve after the point penetrates through the wall of the body cavity. The trocar device preferably also comprises means for triggering the retracting means upon the distal (forward) motion of the protective sleeve. In the preferred embodiment, the retraction of the point provides a positive tactile signal to the user that the skin has been penetrated.

Thus, the trocar of the present invention begins to retract the trocar point away from the underlying organs after the point penetrates through the skin, keeping the point further away from the organs. Furthermore, because of this retraction of the point, the point of the trocar of the present invention is covered more quickly than the point of a similar device that relies solely on the distal (forward) movement of a protective sleeve to cover the point. Finally, since the device can provide a positive signal to the surgeon when the skin has been penetrated, the surgeon knows when to stop advancement of the trocar. Thus, it is believed that the trocar of this invention reduces the risk of accidental organ puncture.

These and other features and advantages will be in part apparent, and in part pointed out hereinafter.

BRIEF DESCRIPTION OF THE DRAWINGS

FIG. 5 is an enlarged partial side elevation view of the trocar, similar to FIG. 2, showing the trocar as it is penetrating the wall of a body cavity;

FIG. 6 is an enlarged partial side elevation view of the trocar, similar to FIG. 2, showing the trocar after it has penetrated the wall of the body cavity;

FIG. 7 is a partial transverse cross-sectional view of the trocar taken along the plane of line 7—7 in FIG. 6;

FIG. 10 is a partial longitudinal cross-sectional view of the second embodiment taken along the plane of line 10—10 in FIG. 8;

FIG. 11 is a partial longitudinal cross-sectional view of the second embodiment, similar to FIG. 10, with the protective sleeve partially retracted;

FIG. 12 is a partial longitudinal cross-sectional view of the second embodiment, similar to FIG. 10, with the protective sleeve fully retracted; and FIG. 13 is a partial longitudinal cross-sectional view of the second embodiment, similar to FIG. 10, with the obturator fully retracted.

Corresponding reference numerals indicate corresponding parts throughout the several views of the drawings.

DETAILED DESCRIPTION OF THE PREFERRED EMBODIMENT

Figure 1:
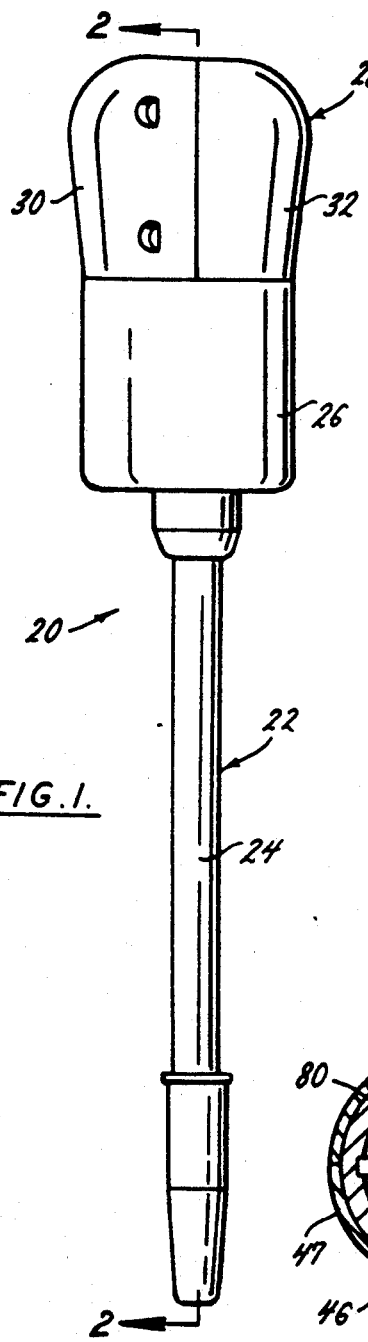
FIG. 1 is side elevation of a trocar constructed according to the principles of this invention.
Figure 3:
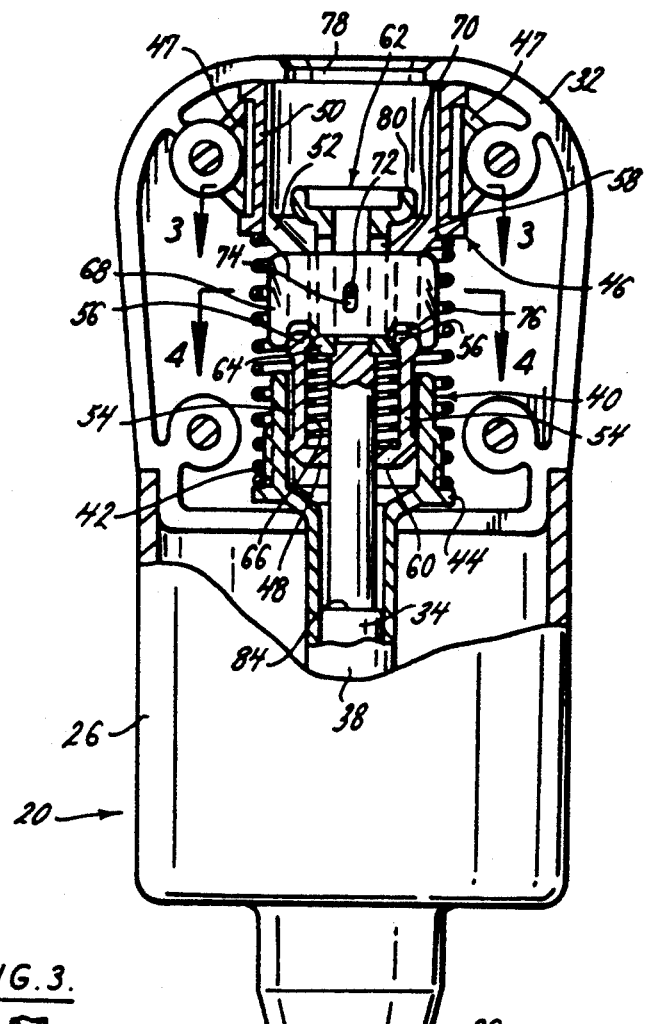
FIG. 3 is a partial transverse cross-sectional view of the trocar taken along the plane of line 3—3 in FIG. 2.
Figure 3:
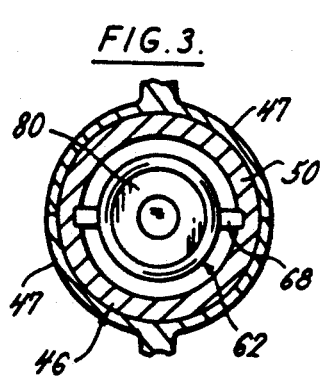
Figure 4:
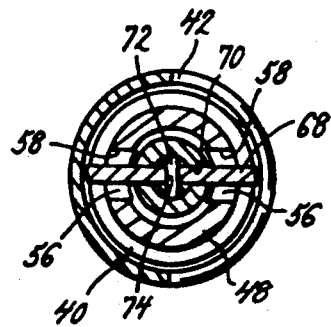
FIG. 4 is a partial transverse cross-sectional view of the trocar taken along the plane of line 4—4 in FIG. 2.

A first embodiment of a trocar device constructed according to the principles of this invention, indicated generally as 20, is shown in side elevation in FIG. 1. The trocar device 20 is of the type placed in the lumen of a cannula to facilitate inserting the cannula through the wall of a body cavity, for example inserting access tube 22 through an abdominal wall. The access tube 22 comprises a cannula 24 that has an enlarged generally funnel-shaped fixture 26 its proximal end. The access tube 22 provides an entryway for laparoscopes, and other surgical instruments. As is know in the art, the access tube 22 may include means (not shown) for supplying pressurized gas to the abdomen. The access tube 22 may also include a trap-door valve at the proximal end of the cannula 24 to prevent the escape of gas through the cannula when it is not occluded by the trocar or a surgical instrument.

Figure 2:
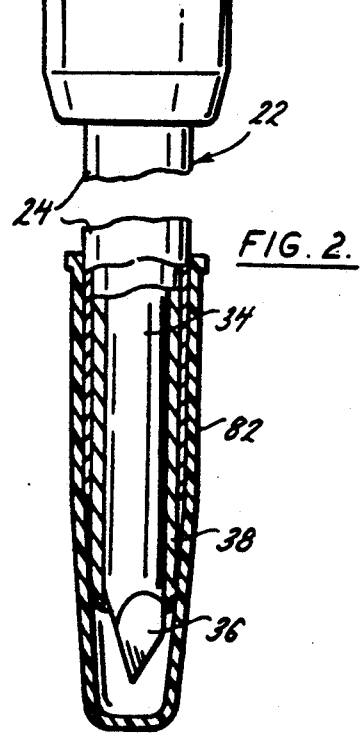
FIG. 2 is an enlarged partial side elevation of the trocar of FIG. 1 (prior to use), rotated about its axis 90°, with part of its casing removed and with portions of the tip broken away to reveal details of construction.

The trocar 20 generally comprises a handle 28, formed from two interfitting casing members 30 and 32 that are secured together with screws or other suitable fastening means. The handle 28 has a generally rounded configuration that can be comfortably gripped by the user. As best shown in FIGS. 2, 5, and 6, the trocar 20 has an obturator 34 extending from the handle 28. The distal end of the obturator 34 has a point 36 for piercing the wall of the body cavity.

A protective sleeve 38 is mounted concentrically around the obturator 34 for axial movement relative thereto. The protective sleeve 38 is resiliently biased distally (relative to the trocar). There are a number of suitable means for biasing the protective sleeve 38, for example, as in this preferred embodiment, the protective sleeve 38 can be biased with a spring. The proximal end of the sleeve 38 can be provided with an enlarged, generally cylindrical end section 40. A coil spring 42 can be mounted generally over the end section 40, extending between an annular flange 44 on the end section 40, and a portion of a generally bell-shaped assembly 46 (described in more detail below). The assembly 46 is engaged by raised ribs 47 on the interior of the casing members 30 and 32, which hold the assembly in place. The action of the spring 42 between the assembly 46 and the protective sleeve 38 resiliently biases the protective sleeve distally. Of course some other type of resilient biasing means could be used so long as protective sleeve 38 can retract proximally as the trocar 20 is being advanced through the wall of the body cavity, yet advance distally after the point 36 (and more specifically the cannula 24) has penetrated through the wall of the body cavity.

The trocar 20 also comprises means for retracting the point 36 of the obturator 34 relative to the protective sleeve 38 after the point has penetrated through the wall of the body cavity, thereby reducing the risk that the point will cause damage inside the body cavity. The trocar 20 preferably comprises means for triggering this retracting means upon the distal (forward) movement of the protective sleeve 38, which occurs after the cannula has penetrated through the wall of the body cavity.

The bell shaped assembly 46 comprises a cup-shaped section 48 at its distal end, a hollow, generally cylindrical section 50, at its proximal end, and a hollow, generally tapering intermediate section 52 in between. The cup-shaped section 48 comprises at least two resilient fingers 54 attached at their distal ends generally adjacent the distal end of the assembly 46, and extending generally proximally. The proximal ends of the fingers 54 are resiliently biased radially outwardly, and are provided with beads 56, discussed below. The proximal end of the generally cylindrical section 50 abuts the casing members that form the handle, while the distal end of the cylindrical section 50 supports the spring 42 as described above. The ribs 47 engage the cylindrical section 50 to anchor the assembly 46 within the handle. The intermediate section 52 has longitudinally extending slots 58, as described below.

The portion of the obturator 34 adjacent the proximal end extends through an opening in the distal end 60 of the bell-shaped assembly 46. A generally spool-shaped cap 62 is secured on the proximal end of the obturator 34. The distal end of the cap 62 has a raised annular shoulder 64 that can be engaged by the beads 56 on the fingers 54. A coil spring 66 is mounted over the portion of the obturator 34 adjacent the distal end, proximal to the distal end of the assembly 46. One end of the spring 66 is engaged by the distal end of the assembly 46, the other end of the spring is engaged by the shoulder 64. The spring 66 thus biases the obturator proximally (with respect to the trocar). Before use, as shown in FIG. 2, the beads 56 on the fingers 54 engage the shoulder 64 to hold the spring 66 in compression. A locking member 68 releasably holds the fingers radially inwardly, locking the fingers 54 in engagement with the shoulder 64. The locking member 68 is preferably flat, and slidably mounted in a slot 70 in the intermediate portion of the cap 62. A pin 72 extends through a longitudinally extending slot 74 in the looking member 68 to retain the looking member in the slot 70 in the cap 62, while permitting the locking member to move longitudinally (i.e., proximally and distally). The sides of the locking member 68 project through the slot 58 in the intermediate section 52 of assembly 46. The bottom edge of the locking member 68 has notches 76, which, when the locking member is in its most distal position (see FIG. 1), receive the ends of the fingers 54 and hold the beads 56 in engagement with the shoulder 64.

The proximal end 40 of the protective sleeve 38 is sized and positioned to engage the locking member 68, and slide the looking member proximally as the protective sleeve moves proximally. The sidewalls of the end section 40 of the protective sleeve 38 are sized to engage the fingers 54, and hold the beads 56 in engagement with the shoulder 64 after the looking member 68 has been displaced. (See FIG. 5). Thereafter, when the protective sleeve 38 moves distally, as occurs after the cannula 24 has penetrated through the wall of the body cavity and the drag of the skin on the sleeve is eliminated, the spring 42 urges the protective sleeve distally. As the end section 40 moves distally, it releases the fingers 54 which spring radially outwardly, causing the beads 56 to clear their engagement with the shoulder 64. This releases the spring 66, allowing it to expand and urge the obturator 34 (and thus point 36) proximally, i.e., retracting the point relative to the trocar 20. (See FIG. 6).

The proximal end of the handle 28 preferably has an opening 78 therein so that the enlarged proximal end 80 of the cap 62 can protrude therethrough when the obturator 34 is in its retracted position. The proximal end 80 strikes the palm of the hand of the user when the obturator 34 retracts. Thus, in addition to an audible signal from the operation of the mechanism, the retraction of the obturator 34 provides a tactile signal that the point 36 has penetrated through the wall of the body cavity, thereby alerting the user to stop advancing the trocar.

A second embodiment of a trocar device is indicated generally as 100 in FIGS. 8-13. The trocar 100 is similar in construction to trocar 20 of the first embodiment, and is likewise adapted for facilitating inserted a cannula through the wall of the body cavity, for example inserting an access tube 102 through the abdominal wall. The access tube 102 comprises a cannula 104 that has an enlarged fixture 106 at is proximal end. The fixture 106 comprises a chamber 108. There is an opening 110 at the proximal end of the chamber through which the trocar fits while the access tube is being inserted in the body cavity, and through which surgical instruments can access the interior of the body cavity after the access tube is in place and the trocar is removed. A trap door valve member 112, having a sealing gasket 114 is pivotally mounted adjacent the opening 110 to close the opening 110. The valve member 112 is operated by a pushbutton 116 in the sidewall of the fixture 106. The pushbutton 116 is reciprocally mounted in a sealing gasket 118, and is resiliently spring-biased outwardly by spring 120. A link 122 extends from the pushbutton 116 to the valve member 112, so that pushing the pushbutton inwardly moves the valve member 112 open, and the action of the spring 120 causing the button to move outwardly when it is released causes the valve member 112 to close.

The chamber 108 also has a Roberts valve 124, by which pressurized gas can be provided to the chamber to maintain the gas pressure in the body cavity, and thereby keep the cavity inflated to facilitate the procedure.

Figure 8:
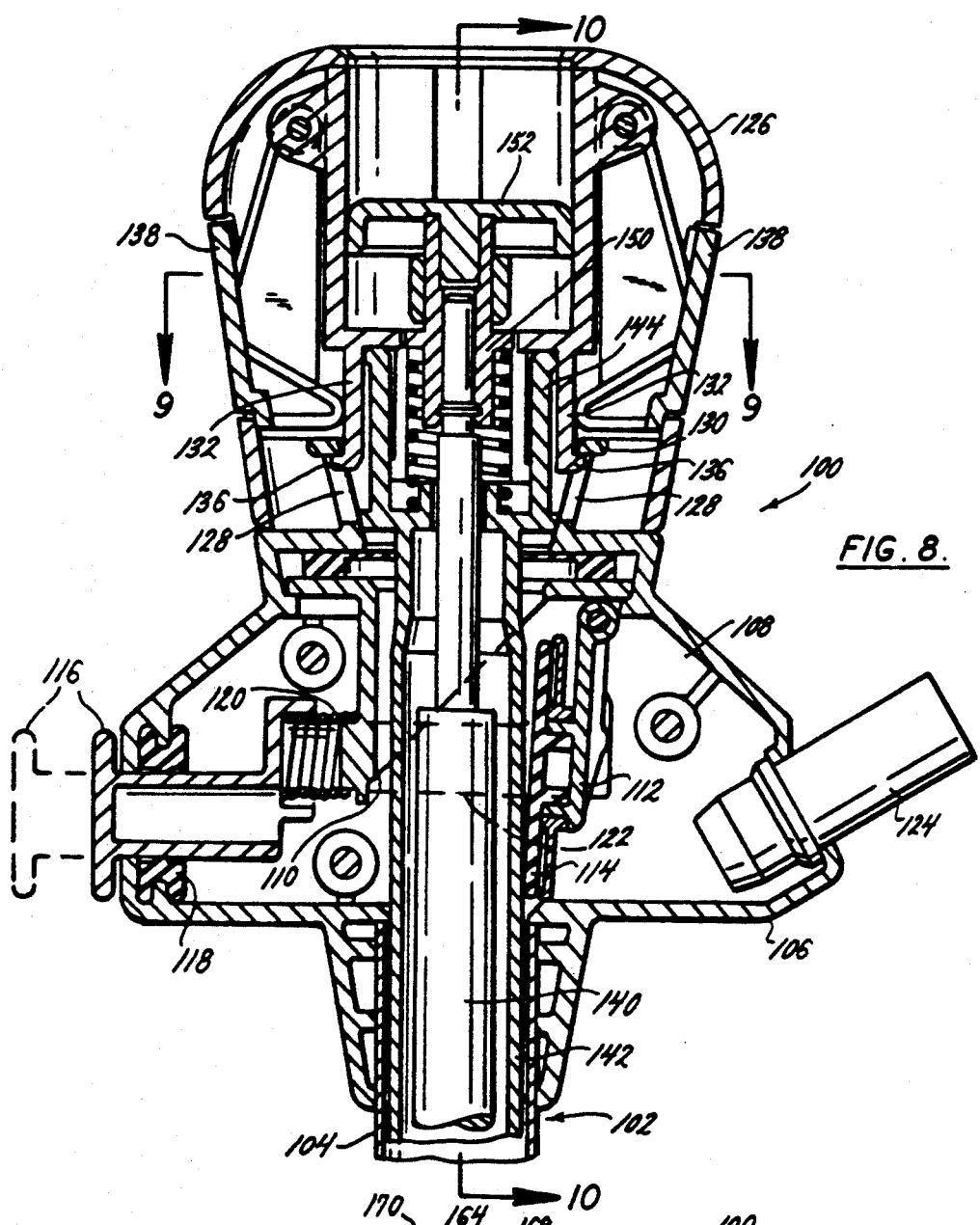
FIG. 8 is a partial longitudinal cross-sectional view of a second embodiment of a trocar constructed according to the principles of this invention.
Figure 9:
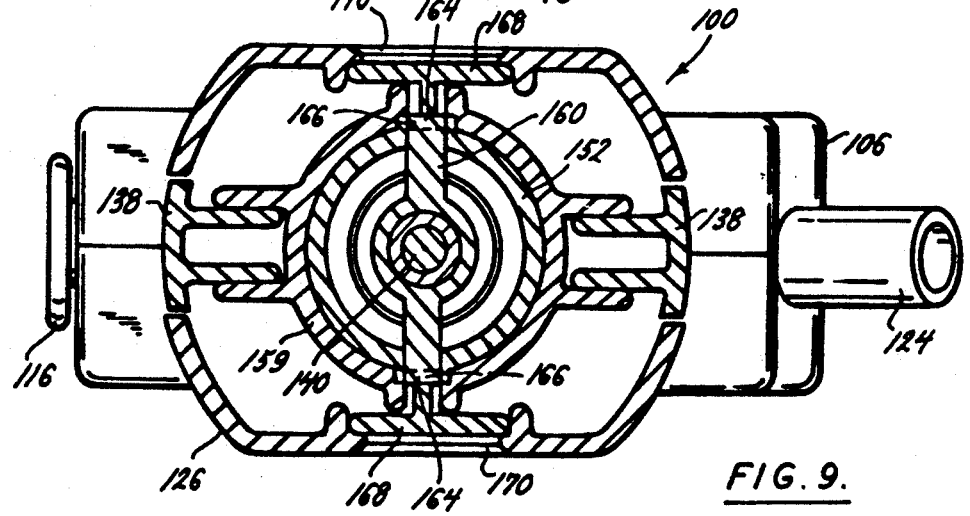
FIG. 9 is a partial transverse cross-sectional view of the second embodiment, taken along the plane of line 9—9 in FIG. 8.

The trocar 100 comprises a handle 126, with a generally rounded configuration that can be comfortably gripped by the user. The handle is releasably attached to the fixture 106 so that after the trocar 100 inserts the access tube 102 in the wall of the body cavity, the trocar can be removed so that the access tube can be used to introduce surgical instruments into the body cavity. The proximal end of the fixture 106 has a funnel-shaped extension 128, with an enlarged rim 130. As shown in FIG. 8, the distal end of the handle 126 has resilient fingers 132 that extend into slots in the wall of the extension 128 and have a shoulder 136 to engage the rim 130 and attach the handle 126 to the fixture 106. The sides of the handle have two pivotally mounted buttons 138 which, when depressed, push the fingers 132 inwardly, out of engagement with the rim so that the handle 126 and the fixture 106 can be separated.

The trocar 100 also includes an obturator 140 extending from the distal end of the handle 126. The distal end of the obturator has a point, like the point 36 on obturator 34. A protective sleeve 142 is mounted around the obturator 140 for axial movement relative thereto. The protective sleeve 142 is resiliently biased distally (relative to the trocar 100). In this second preferred embodiment, the protective sleeve 142 is biased with a spring. The proximal end of the sleeve 142 is provided with an enlarged generally cylindrical section 144. A coil spring 146 is mounted inside the cylindrical section 144, with its distal end supported in an internal shoulder 148 on the sleeve, and its proximal end engaging a raised shoulder on the obturator (described in more detail below). The action of the spring 146 resiliently biases the protective sleeve 142 distally. However, the protective sleeve can move proximally against the bias, under the forces applied by the wall of the body cavity as the trocar is advanced through the wall of the body cavity, and resilient move distally when the applied forces are removed, as occurs once the cannula 104 is inserted through the wall of the body cavity and the protective sleeve is no longer in frictional contact with the wall of the body cavity. Of course as noted above in the description of the first embodiment, some resilient biasing means other than coil spring 146 could be used.

The trocar 100 also comprises means for retracting the point on the obturator 140 relative to the protective sleeve 142 after the point has penetrated through the wall of the body cavity, thereby reducing the risk that the point will cause damage inside the body cavity. In this second embodiment, the retracting means is triggered upon the distal (forward) movement of the protective sleeve 142.

As best shown in FIGS. 10-13, there is a tubular extension 150 secured on a shoulder on the proximal end of the obturator 140. An enlarged head 152 is secured onto the proximal end of the extension 150. The extension 150 has a generally radially extending flange 154. The distal surface of the flange 154 forms the shoulder that engages the proximal end of the spring 146. There are at least two proximally extending resilient fingers 156 around the obturator. The proximal ends of the fingers 156 are resiliently biased outwardly from the obturator, and have beads 158 that can engage the flange 154 on the extension 150, and thereby hold the obturator against proximal retraction under the bias of spring 146. The distal ends of the fingers 156 are anchored to a ring 157. The ring 157 is supported on a generally cylindrical base 159, similar to the bell-shaped assembly 46 of the first embodiment.

Before use, as shown in FIG. 10, the beads 158 on the fingers 156 engage the flange 154, holding the spring 146 in compression and holding the obturator 140 from proximal retraction. A looking member 160, slidably mounted on the proximal portion of the extension member 150, locks the fingers 156 in engagement with the flange 154. The bottom edge of the locking member 160 has notches 162 which when the looking member 160 is in its distal most position, receive and engage the fingers 156 and hold the beads 158 in engagement with the shoulder.

The cylindrical section 144 of the protective sleeve 142 is sized and positioned to engage the locking member 160, and slide the locking member proximally as the protective sleeve slides proximally (as occurs as the trocar 100 is advanced through the wall of a body cavity and the friction of the wall acts against the protective sleeve 142). The locking member 160 has tabs on 164 on opposite sides that are trapped between and can engage portions 166 of indicators 168. The indicators are slidably mounted on opposite sides of the handle 126. There are windows 170 on opposite sides of the sidewall of the handle 126, each exposing a portion of one of the indicators 168. The indicator can have indicia at locations 172a and 172b to provide a visual indication of the status of the trocar 100. The indicia at 172a is visible through the windows 170 when the trocar is ready for use (FIG. 10). The indicia at 172b is visible through the windows 170 when the trocar point is retracted, as described in detail below (FIG. 13). The tabs 164 can move within the portions 166 of the indicator 168. This allows extra motion or dwell that facilitates resetting the device, as described below.

As shown in FIG. 11, when the protective sleeve 142 moves proximally, it pushes the locking member 160 proximally until the tabs 164 engage the portions 166 of the indicators 168. Thereafter, further proximal movement of the protective sleeve 142 not only moves the locking member 160, but it also moves the indicators 168. The cylindrical section 144 of the protective sleeve 142 is sized to engage the fingers 156, and hold the beads 158 in engagement with the flange 154 after the locking member 160 has been displaced. Thus, as shown in FIG. 12, when the protective sleeve 142 is in its fully retracted position, the locking member 160 has been moved proximally, and the walls of the cylindrical section 144 hold the fingers 156 in engagement with the flange 154. The mechanism of the trocar 100 is now primed so that any distal advancement of the protective sleeve will trigger the trocar to retract the obturator point.

When the cannula 104 pierces through the wall of the body cavity, it shields the protective sleeve 142 from contact with the wall of the body cavity, and thus the wall of the body no longer exerts frictional force on the protective sleeve. The reduction in force on the sleeve allows the protective sleeve 142 to advance distally under the bias of spring 146. As the protective sleeve advances, the cylindrical section 144 releases the fingers 156. When the fingers 156 are released, they spring resiliently outwardly, and the beads 158 clear the flange 154. This allows the obturator 140 to retract under the bias of the spring 146. As the obturator retracts, it moves the locking member 160 with it, which in turn moves the indicator so that the indicia at 172b is visible through the window 170, providing a visible indication that the obturator point has retracted. Moreover, the cap 152 protrudes through an opening 174 in the handle 126 providing an additional visible signal, as well as a tactile signal that the obturator point has retracted. A rim 176 around the cap 152 engages the periphery of the opening 174 to allow the cap 152 to protrude through the opening 174, but not pass completely through. A shoulder 178 may also be provided on the obturator to engage the a shoulder 180 on the protective sleeve 142, and limit the retraction of the obturator.

OPERATION

The trocar 20 is prepared for use by removing the protective cap 82 over the point. The access tube 22 is already installed over the distal end of the trocar 20. The user grasps the handle 28 of the trocar 20, with the palm of the hand over the proximal end. The trocar 20 is advanced against the wall of a body cavity, for example the abdomen. As the trocar 20 is advanced, friction or drag from the skin urges the protective sleeve 38 proximally. As the protective sleeve 38 moves proximally, its enlarged proximal end 40 also moves proximally. The proximal end 40 of the protective sleeve 38 pushes the looking member 68 proximally, releasing the notches 76 from their engagement with the fingers 54, while the enlarged end 40 simultaneously moves over the fingers to continue to hold the beads 56 in engagement with the shoulder 64. (Compare FIGS. 2 and 5.) The user continues to advance the trocar, penetrating the wall of the body cavity. Once the cannula 24 has penetrated through the wall of the body cavity, the drag on the protective sleeve 38 is reduced, and the spring 42 urges the protective sleeve 38 distally. The distal motion of the sleeve 38 also causes the enlarged end to move distally, releasing the fingers 54. The fingers 54 spring radially outwardly, releasing beads 56 from their engagement with the shoulder 64. This allows the spring 66 to expand, pushing the obturator 34 proximally. (Compare FIGS. 5 and 6.) Thus the point 36 begins to move proximally, i.e., it retracts. The proximal motion of the point 36 causes the point to be quickly surrounded by the protective sleeve. As the obturator retracts, the proximal end 80 of the cap 62 projects through the opening 78 in the handle 28, nudging the palm of the user and providing a positive tactile signal that the trocar has penetrated the wall of the body cavity. Thus the user knows when to stop advancing the trocar 20.

As shown in FIG. 6, the obturator 34 preferably has a shoulder 84, which engages the distal end 60 of the assembly 46, thereby limiting the proximal movement of the obturator 34.

The user then grasps the fixture 26 of the access tube 22, and pulls the trocar proximally, leaving the access tube in the abdominal wall. As noted above, the access tube preferably has a trap-door valve that closes the cannula 24 when the trocar is withdrawn to prevent the escape of gas from the abdomen. The trocar can be quickly prepared for reuse (on the same patient) by pressing the enlarged end 80 of the cap 62 down through the opening 78, until the beads 56 on the fingers 54 engage the shoulder 64, and the notches 76 on the looking member 68 hold the fingers in place. Another access tube can be placed over the trocar 20, and the procedure repeated.

The trocar 100 is prepared for use by removing the protective cap over the point. The access tube 102 is already installed over the distal end of the trocar 100. The user grasps the handle 126 of the trocar 100, with the palm of the hand over the end. The trocar 100 is advanced against the wall of a body cavity, for example the abdomen. As the trocar 100 is advanced, friction or drag from the skin urges the protective sleeve 142 proximally. The proximal movement of the protective sleeve pushes the locking member 160 proximally, until the cylindrical section 144 displaces the locking member and holds the fingers 156 in engagement with the flange 154. Compare FIGS. 10 and 12. The trocar is now primed and ready to retract the obturator.

The user continues to advance the trocar until the cannula 104 pierces completely through the wall of the abdomen. At this point, the cannula 104 shields the protective sleeve 142 from frictional contact with the skin, and the protective sleeve begins to advance distally. As the protective sleeve advances distally, the cylindrical section 144 uncovers the fingers 156, which spring resiliently outwardly. When the beads 158 on the fingers 156 clear the flange 154, the obturator 140 begins to retract under the bias of the spring 146. The retraction of the obturator causes the indicator 168 to slide so that the indicia at 172b is exposed in the window 170. Furthermore the cap 152 protrudes through the opening 174 in the handle 126, giving both a visual and tactile signal that the trocar has pierced through the wall of the abdomen, so that further advancement can be halted.

The cannula is then moved to its desired position. The fixture 106 is gripped, and the buttons 138 depressed to release the handle from the fixture. The trocar can then be pulled from the access tube 102. As the trocar is removed from the fixture, the trap door valve member 112 closes the opening 110 to prevent the escape of the gas used to inflate the abdomen. Instruments can be introduced into the abdomen via the access tube 102. Lost gas can be replaced via the Roberts valve 124, excess gas can be vented by pressing pushbutton 116 to open valve member 112.

The trocar 100 can be reset by pressing the end cap 152. This pushes the obturator distally and brings the flange 154 below the beads on the fingers. The locking member 160 is freely slidable with respect to the extension 150 so that when the cap 152 is pressed, the obturator 140 and the extensions 150 move distally relative to the locking member 160 so that the shoulder 154 on the extension 150 is brought into engagement with the fingers 156 before the locking member 160 engages the fingers. Preferably the locking member 160 will frictionally engage some portion of the mechanism, retarding the locking member 160, and facilitating this relative motion. The obturator can overtravel enough that further pushing brings the locking member 160 over the fingers, holding the beads 158 in engagement with the flange 154. The tabs 164 on the locking member 160 engage the portion 166 of the indicator 168 and restore the indicators to their initial positions. The trocar is now ready for installation in another access tube for reuse (on the same patient).

As various changes could be made in the above constructions without departing from the scope of the invention, it is intended that all matter contained in the above description or shown in the accompanying drawings shall be interpreted as illustrative and not in a limited sense.

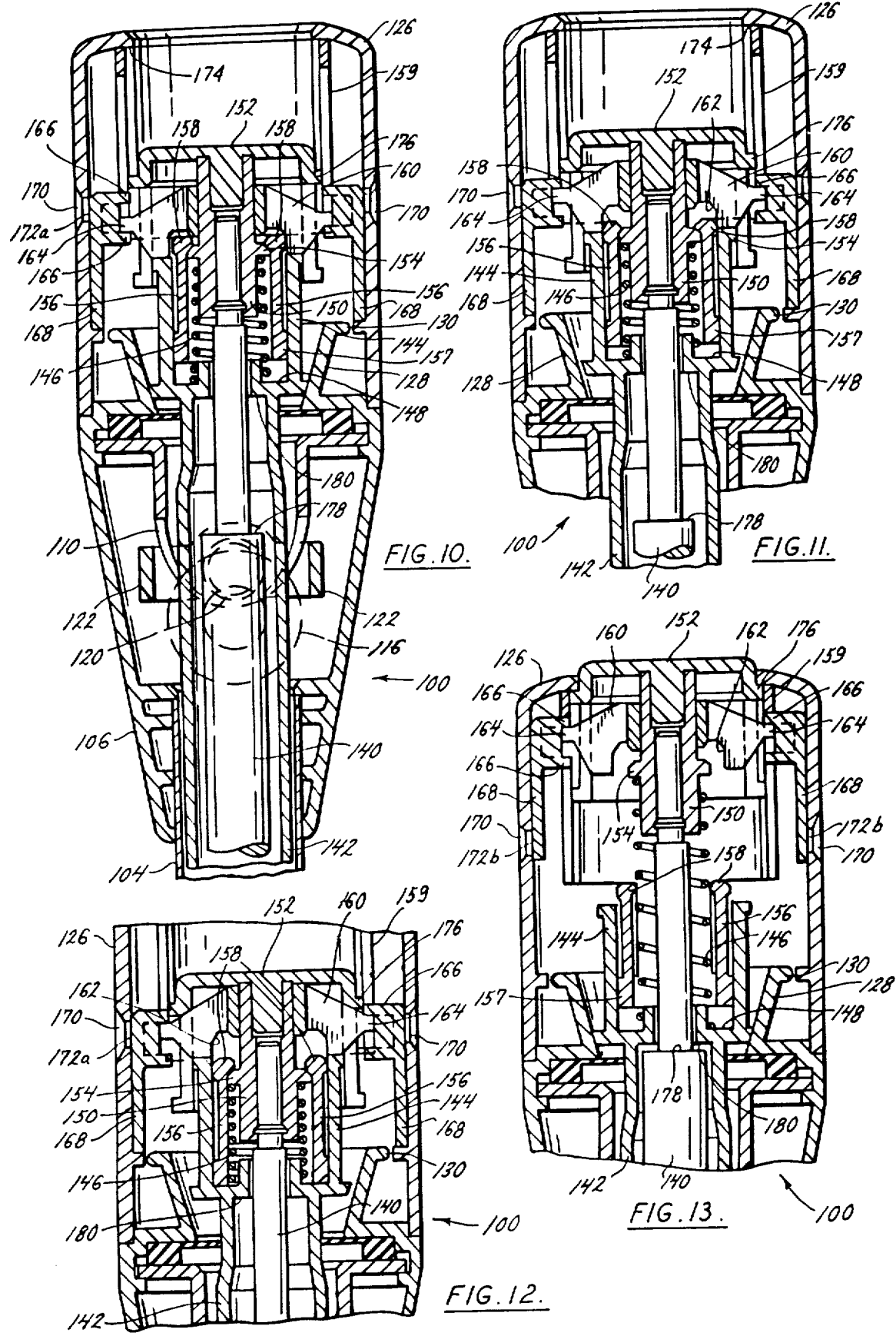

What is claimed is:

1. A trocar for placement in the lumen of a cannula to facilitate inserting the cannula through the wall of a body cavity, the trocar comprising a handle, an obturator with a point for piercing the wall of the body cavity, and a protective sleeve mounted concentrically around the obturator, the obturator retracting proximally relative to the handle generally simultaneously as the protective sleeve advances distally relative to the handle after the trocar point has penetrated through the wall of the body cavity.

2. The trocar according to claim 1 wherein the protective sleeve advances distally with respect to the obturator after the trocar point penetrates through the wall of the body cavity, and wherein the obturator retracts proximally upon the distal advancement of the protective sleeve.

3. A trocar for placement in the lumen of a cannula to facilitate inserting the cannula through the wall of a body cavity, the trocar having a housing, an obturator with a point for piercing the wall of the body cavity, and a protective sleeve mounted concentrically around the obturator, and means for retracting the obturator proximally relative to the housing at approximately the same time the protective sleeve advances distally relative to the housing after the trocar point has penetrated through the wall of the body cavity.

4. The trocar according to claim 3 wherein the retracting means retracts the obturator after the cannula has penetrated through the wall of the body cavity.

5. The trocar according to claim 4 wherein the trocar comprises means for advancing the protective sleeve distally relative to the obturator after the trocar point has penetrated through the wall of the body cavity, and means for triggering the retracting means upon the relative distal advancement of the protective sleeve.

6. The trocar according to claim 5 wherein the protective sleeve can move axially with respect to the obturator, and is resiliently biased distally so that the protective sleeve can retract proximally relative to the obturator in response to drag from the wall of the body cavity as the trocar is advanced through the wall of the body cavity, and can advance distally after the cannula has penetrated through the wall of the body cavity and reduced the drag on the sleeve, and further comprising means for triggering the retracting means upon the distal advancement of the protective sleeve.

7. The trocar according to claim 4 wherein the protective sleeve can move axially with respect to the obturator, and is resiliently biased distally so that the protective sleeve can retract proximally relative to the obturator in response to drag from the wall of the body cavity as the trocar is advanced through the wall of the body cavity, and can advance distally after the cannula has penetrated through the wall of the body cavity and reduced the drag on the sleeve, and further comprising means for triggering the retracting means after the proximal retraction of the protective sleeve that occurs while the trocar is penetrating the wall of the body cavity, and the subsequent distal advancement of the protective sleeve that occurs after the cannula has penetrated through the wall of the body cavity.

8. The trocar according to claim 4 further comprising means for providing a tactile signal to the user when the obturator retracts, to signal the user that the trocar point has penetrated through the wall of the body cavity.

9. A trocar for placement in the lumen of a cannula to facilitate inserting the cannula through the wall of a body cavity, the trocar comprising:
a handle;
an obturator extending distally from the handle and having a point on its distal end for piercing the wall of the body cavity;
a protective sleeve mounted concentrically around the obturator for axial movement relative to the obturator, and resiliently biased distally so that the protective sleeve can retract proximally relative to the obturator in response to drag from the wall of the body cavity as the trocar point is advancing through the wall of the body cavity, and can advance distally after the cannula has penetrated through the wall of the body cavity and reduced the drag on the protective sleeve; and
means for retracting the obturator relative to the handle generally at the same time the protective sleeve advances distally relative to the handle after the trocar point has penetrated through the wall of the body cavity.

10. The trocar according to claim 9 further comprising means, responsive to the distal advancement of the protective sleeve for triggering the retracting means.

11. The trocar according to claim 10 further comprising means for preventing the triggering means from triggering the retracting means until after the protective sleeve has retracted proximally relative to the obturator, such as is caused by advancing the trocar through the wall of the body cavity, wherein the triggering occurs after the protective sleeve first moves proximally relative to the handle and then moves distally relative to the handle.

12. The trocar according to claim 9 further comprising releasable locking means for preventing actuation of the retracting means, and means, associated with the protective sleeve, for releasing the releasable locking means upon the proximal retraction of the protective sleeve, wherein the triggering occurs after the protective sleeve first moves proximally relative to the handle and then moves distally relative to the handle.

13. The trocar according to claim 12 further comprising means associated with the protective sleeve for temporarily preventing the operation of the retracting means after the proximal retraction of the protective sleeve releases the releasable locking means, until the distal advancement of the protective sleeve.

14. The trocar according to claim 9 wherein there is an opening in the handle, and further comprising means, associated with the obturator, that protrudes through the opening when the obturator is in its retracted position.

15. A trocar for placement in the lumen of a cannula to facilitate inserting the cannula through the wall of a body cavity, the trocar comprising:
a handle;
an obturator extending distally from the handle and having a point on its distal end for piercing the wall of the body cavity;
a protective sleeve mounted concentrically around the obturator for axial movement relative to the obturator, and resiliently biased distally so that the protective sleeve can retract proximally relative to the obturator in response to drag from the wall of the body cavity as the trocar point is advancing through the wall of the body cavity, and can advance distally after the cannula has penetrated through the wall of the body cavity and reduced the drag on the protective sleeve;
biasing means for biasing the obturator proximally relative to the protective sleeve;
means for releasably securing the obturator from proximal retraction under the bias of the biasing means; and
means for releasing the releasable securing means upon the proximal retraction of the protective sleeve that occurs while the trocar is advancing through the wall of the body cavity, and the subsequent distal advancement of the protective sleeve that occurs after the cannula has penetrated through the wall of the body cavity.

16. The trocar of claim 15 where the releasable securing means comprises means for engaging the obturator, and means for releasably locking the engaging means in engagement with the obturator, and wherein the means for releasing the releasable securing means comprises means, associated with the protective sleeve for releasing the releasable locking means upon proximal retraction of the sleeve, and means for temporarily holding the engaging means in engagement with the obturator until the distal advancement of the sleeve.

17. The trocar according to claim 15 wherein there is an opening in the handle, and further comprising means, associated with the obturator, that protrudes through the opening when the obturator is in its retracted position.

* * * * *

UNITED STATES PATENT AND TRADEMARK OFFICE
CERTIFICATE OF CORRECTION

PATENT NO. : 5,152,754
DATED : October 6, 1992
INVENTOR(S) : Alan K. Plyley, John M. Barker, Claude Vidal and Russell J. Redmond It is certified that error appears in the above-indentified patent and that said Letters Patent is hereby corrected as shown below:

In the Drawings:

Figures 10 and 11 should be deleted to be replaced with figures 10 and 11 as shown on the attached sheet.

Col. 4, line 38, delete "looking" insert --locking--.
Col. 4, line 39, delete "looking" insert --locking--.
Col. 4, line 54, delete "looking" insert --locking--.

Col. 6, line 43, delete "looking" insert --locking--.
Col. 6, line 47, delete "looking" insert --locking--.

Col. 7, line 61, delete "looking" insert --locking--.
Col. 8, line 32, delete "looking" insert --locking--.

Signed and Sealed this

Twenty-sixth Day of April, 1994

Attest:

BRUCE LEHMAN

*Attesting Officer*   Commissioner of Patents and Trademarks